US00PP26854P2

(12) United States Plant Patent
Kitahara

(10) Patent No.: US PP26,854 P2
(45) Date of Patent: Jun. 21, 2016

(54) ***PHLOX* PLANT NAMED 'PHL090201'**

(50) Latin Name: *Phlox hybrida*
Varietal Denomination: PHL090201

(71) Applicant: Akiko Kitahara, Mizuho (JP)

(72) Inventor: Akiko Kitahara, Mizuho (JP)

(73) Assignee: EuroAmerican Propagators LLC, Bonsall, CA (US)

( * ) Notice: Subject to any disclaimer, the term of this patent is extended or adjusted under 35 U.S.C. 154(b) by 42 days.

(21) Appl. No.: 14/121,656

(22) Filed: Oct. 1, 2014

(51) Int. Cl.
*A01H 5/02* (2006.01)

(52) U.S. Cl.
USPC ..... Plt./320

(58) Field of Classification Search
USPC ..... Plt./320
See application file for complete search history.

*Primary Examiner* — Anne Grunberg
(74) *Attorney, Agent, or Firm* — C. A. Whealy

(57) ABSTRACT

A new and distinct *Phlox* plant named 'PHL090201', characterized by its upright, outwardly spreading and mounding plant form; vigorous growth habit; freely branching habit and short internodes; dense and bushy plant form; early and freely flowering habit; dark lavender-colored flowers; long flowering period; and relatively resistant to Powdery Mildew.

1 Drawing Sheet

Botanical designation: *Phlox hybrida.*
Cultivar denomination: 'PHL090201'.

BACKGROUND OF THE INVENTION

The present invention relates to a new and distinct *Phlox* plant, botanically known as *Phlox hybrida* and hereinafter referred to by the name 'PHL090201'.

The new *Phlox* plant is a product of a planned breeding program conducted by the Inventor in Higashiomi, Shiga, Japan. The objective of the breeding program is to create new vigorous and mounding *Phlox* plants with early flowering habit and long flowering period.

The new *Phlox* plant originated from a cross-pollination made by the Inventor on May 28, 2007 in Higashiomi, Shiga, Japan of a proprietary selection of *Phlox hybrida* identified as code number 07FL-02, not patented, as the female, or seed, parent with an unnamed selection of *Phlox divaricata,* not patented, as the male, or pollen, parent. The new *Phlox* plant was discovered and selected by the Inventor as a single flowering plant within the progeny of the stated cross-pollination in a controlled environment in Higashiomi, Shiga, Japan on Sep. 10, 2008.

Asexual reproduction of the new *Phlox* plant by vegetative cuttings in a controlled greenhouse environment in Higashiomi, Shiga, Japan since Sep. 16, 2008 has shown that the unique features of this new *Phlox* plant are stable and reproduced true to type in successive generations.

SUMMARY OF THE INVENTION

Plants of the new *Phlox* plant have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'PHL090201'.

These characteristics in combination distinguish 'PHL090201' as a new and distinct *Phlox* plant:

1. Upright, outwardly spreading and mounding plant form.
2. Vigorous growth habit.
3. Freely branching habit and short internodes; dense and bushy plant form.
4. Early and freely flowering habit.
5. Dark lavender-colored flowers.
6. Long flowering period.
7. Relatively resistant to Powdery Mildew.

Plants of the new *Phlox* differ from plants of the female parent selection in the following characteristics:

1. Plants of the new *Phlox* have broader leaves than plants of the female parent selection.
2. Plants of the new *Phlox* flower earlier than plants of the female parent selection.
3. Plants of the new *Phlox* and the female parent selection differ in flower color as plants of the female parent selection have light lavender pink-colored flowers.

Plants of the new *Phlox* differ from plants of the male parent selection in the following characteristics:

1. Plants of the new *Phlox* have smaller leaves than plants of the male parent selection.
2. Plants of the new *Phlox* and the male parent selection differ in flower color as plants of the male parent selection have blue-colored flowers.
3. Plants of the new *Phlox* flower for a longer period of time than plants of the male parent selection.
4. Plants of the new *Phlox* are more resistant to Powdery Mildew than plants of the male parent selection.

Plants of the new *Phlox* can be compared to plants of the *Phlox subulata*×*Phlox stolonifera* 'PPPHL0604', disclosed in U.S. Plant Pat. No. 23,703. In side-by-side comparisons, plants of the new *Phlox* and 'PPPHL0604' differed in the following characteristics:

1. Plants of the new *Phlox* were taller and more vigorous than plants of 'PPPHL0604'.
2. Plants of the new *Phlox* flowered later than plants of 'PPPHL0604'.

3. Plants of the new *Phlox* and 'PPPHL0604' differed in flower color as plants of 'PPPHL0604' had bright pink-colored flowers.

Plants of the new *Phlox* can be compared to plants of the *Phlox subulata*×*Phlox stolonifera* 'PPPHL07201', disclosed in U.S. Plant Pat. No. 23,705. In side-by-side comparisons, plants of the new *Phlox* and 'PPPHL07201' differed in the following characteristics:

1. Plants of the new *Phlox* were taller and more vigorous than plants of 'PPPHL07201'.
2. Plants of the new *Phlox* flowered earlier than plants of 'PPPHL07201'.
3. Plants of the new *Phlox* and 'PPPHL07201' differed in flower color as plants of 'PPPHL07201' had violet blue-colored flowers.

BRIEF DESCRIPTION OF THE PHOTOGRAPHS

The accompanying colored photographs illustrate the overall appearance of the new *Phlox* plant showing the colors as true as it is reasonably possible to obtain in colored reproductions of this type. Colors in the photographs may differ slightly from the color values cited in the detailed botanical description which accurately describe the colors of the new *Phlox* plant.

The photograph at the bottom of the sheet comprises a side perspective view of typical flowering plants of 'PHL090201' grown in a container.

The photograph at the top of the sheet is a close-up view of a typical flowering plant of 'PHL090201'.

DETAILED BOTANICAL DESCRIPTION

The aforementioned photographs and following observations, measurements and values describe plants grown during the spring in 25-cm containers in an outdoor nursery in Bonsall, Calif. and under cultural practices typical of *Phlox* production. Four plants were planted in a container and the description was taken on single plants. During the production of the plants, day temperature ranged from 16° C. to 27° C., night temperatures ranging from 7° C. to 14° C. and light levels ranging from 5,000 to 8,000 foot-candles. Plants were pinched two times and were five months old when the photographs and description were taken. In the following description, color references are made to The Royal Horticultural Society Colour Chart, 2007 Edition, except where general terms of ordinary dictionary significance are used.

Botanical classification: *Phlox hybrida* 'PHL090201'.

Parentage:

*Female, or seed, parent*.—Proprietary, selection of *Phlox hybrida* identified as code number 07FL-02, not patented.

*Male, or pollen, parent*.—Unnamed selection of *Phlox divaricata,* not patented.

Propagation:

*Type*.—By cuttings.

*Time to initiate roots, summer*.—About one week at temperatures ranging from 17° C. to 29° C.

*Time to produce a rooted plant, summer*.—About four weeks at temperatures ranging from 17° C. to 29° C.

*Root description*.—Thin to medium in thickness; white in color.

*Rooting habit*.—Moderately freely branching; medium density.

Plant description:

*Plant and growth habit*.—Upright, outwardly spreading and mounding plant habit; vigorous growth habit; freely branching habit, about 24 primary laterals each with numerous secondary laterals; relatively short internodes; dense and bushy plant form.

*Plant height*.—About 42 cm.

*Plant width* (*spread*).—About 30 cm.

*Lateral branches*.—Length: About 37 cm. Diameter: About 2 mm. Internode length: About 1.5 cm. Strength: Strong. Texture: Pubescent. Color, developing: Close to 146A. Color, fully developed: Close to 195A to 195B.

Leaf description:

*Arrangement*.—Opposite, simple; sessile.

*Length*.—About 6.7 cm.

*Width*.—About 1.3 cm.

*Shape*.—Lanceolate.

*Apex*.—Acute.

*Base*.—Rounded; clasping.

*Margin*.—Entire.

*Texture, upper surface*.—Scattered pubescence.

*Texture, lower surface*.—Smooth, glabrous.

*Venation pattern*.—Pinnate.

*Color*.—Developing leaves, upper surface: Close to 146A. Developing leaves, lower surface: Close to 146B. Fully expanded leaves, upper surface: Close to 137A; venation, close to 137B. Fully expanded leaves, lower surface: Close to 147B; venation, close to 147C.

Flower description:

*Flower form and flowering habit*.—Single rotate and salverform flowers arranged in small terminal and axillary cymes, each cyme with four to five flowers; flowers face upright to outwardly; freely flowering habit with more than 700 flowers developing per plant.

*Fragrance*.—Moderately fragrant; sweet floral, violet-like.

*Natural flowering season*.—Plants begin flowering about four to six weeks after planting; long flowering period with plants continuously flowering from spring to autumn in California.

*Postproduction longevity*.—Flowers last about four to five days on the plant; flowers not persistent.

*Flower buds*.—Height: About 2 cm. Diameter: About 3 mm. Shape: Elongated oblong. Color: Close to 93D.

*Inflorescence height*.—About 3.4 cm.

*Inflorescence diameter*.—About 4 cm to 6.5 cm.

*Flower diameter*.—About 3 cm.

*Flower depth*.—About 2.2 cm.

*Flower throat diameter*.—About 1.5 mm.

*Flower tube length*.—About 1.7 cm.

*Flower tube diameter, at base*.—About 2 mm.

*Petals*.—Quantity per flower and arrangement: Typically five in a single whorl; petals fused at the base into a narrow tube. Lobe length: About 1.6 cm. Lobe width: About 1 cm. Shape: Obovate. Apex: Erose. Margin: Entire. Texture: Petal lobes, upper surface: Smooth, glabrous. Petal lobes, lower surface: Smooth, glabrous; velvety. Throat: Smooth, glabrous. Tube: Smooth, glabrous. Color: Developing petal lobes, upper surface: Close to 90D. Developing petal lobes, lower surface: Close to 91B. Fully expanded petal lobes, upper surface: Close to 86B; towards the throat, close to 86A; venation, close to 86B; color becoming closer to 90D with development. Fully expanded petal lobes, lower surface: Close to N88C; venation, close to N88C. Flower throat: Close to 86D; venation, close to 86D. Flower tube: Close to 86A to 86B; venation, close to 86A.

*Sepals*.—Quantity per flower and arrangement: Typically five in a single whorl, fused towards the base into a slender tube and reflexed towards the apex. Length: About 8 mm. Width: About 1 mm. Shape: Lanceolate. Apex: Acuminate. Margin: Entire. Texture, upper and lower surfaces: Pubescent. Color, upper and lower surfaces: Close to 147A.

*Peduncles*.—Length: About 4 cm. Diameter: About 1 mm. Angle: Erect to about 45° from vertical. Strength: Strong. Texture: Pubescent. Color: Close to 146A.

*Pedicels*.—Length: About 4 mm. Diameter: Less than 1 mm. Angle: About 30° to 45° from peduncle axis. Strength: Strong. Texture: Pubescent. Color: Close to 146A.

*Reproductive organs*.—Stamens: Quantity per flower: Typically five. Filament length: About 3 mm. Filament color: Close to 92D. Anther shape: Narrowly lanceolate. Anther length: About 1.5 mm. Anther color: Close to 11A. Pollen amount: Moderate. Pollen color: Close to 12A. Pistils: Quantity per flower: One. Pistil length: About 4 mm. Stigma shape: Tri-parted. Stigma color: Close to N144A. Style length: About 2.5 mm. Style color: Close to 145B. Ovary color: Close to 144B.

*Seeds and fruits*.—Seed and fruit development have not been observed on plants of the new *Phlox*.

Disease & pest resistance: Plants of the new *Phlox* have been noted to be relatively resistant to Powdery Mildew. Plants of the new *Phlox* have not been noted to be resistant to pests and other pathogens common to *Phlox* plants.

Garden performance: Plants of the new *Phlox* have been observed to have good garden performance and tolerate rain and wind and to be hardy to USDA Hardiness Zone 5.

It is claimed:

1. A new and distinct *Phlox* plant named 'PHL090201' as illustrated and described.

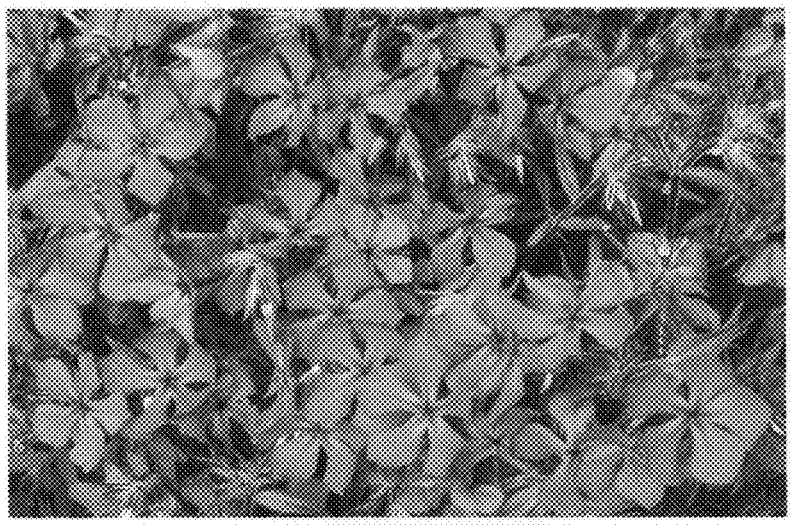
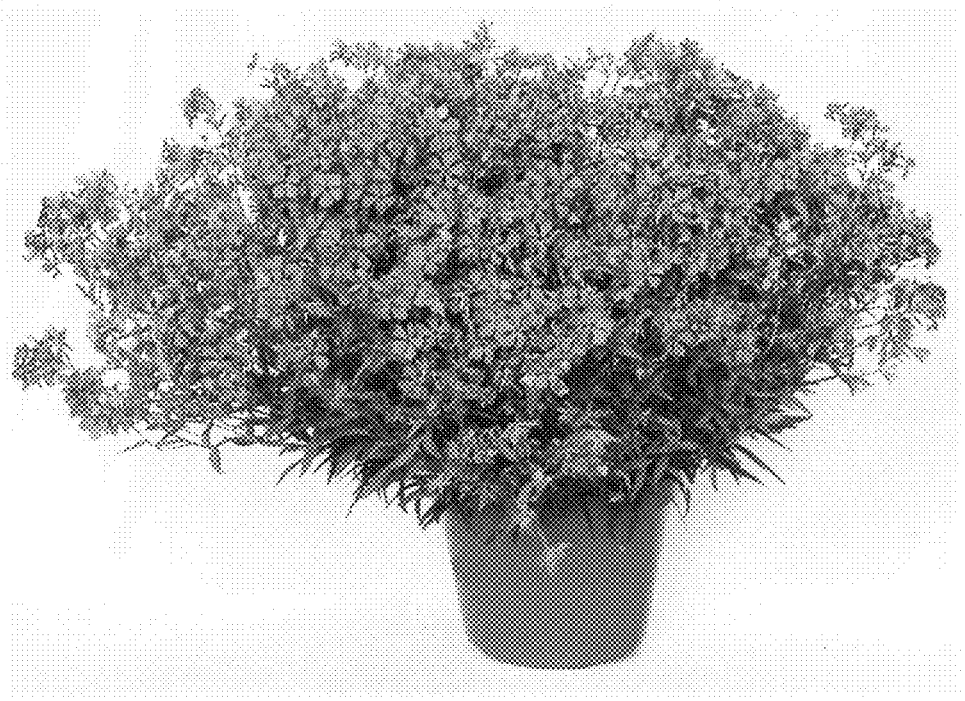

* * * * *